US006887882B2

(12) United States Patent
Eun et al.

(10) Patent No.: US 6,887,882 B2
(45) Date of Patent: May 3, 2005

(54) PHARMACEUTICAL COMPOSITIONS COMPRISING CHELIDONINE OR DERIVATIVES THEREOF

(75) Inventors: Jae-Soon Eun, 105-202, Seoho Apt., 337 Songchundong 1-ga, Deokjin-gu, Chonbuk-si, Chonbuk (KR), 561-765; Yong-Geun Kwak, 113-107, Jinbukwoosung Apt., Jinbuk-dong, Deokjin-gu, Chonju-si, Chonbuk (KR), 561-783; Dae-Keun Kim, 102-205, Dongkuk Apt., 582-1, Yueui-dong, Deokjin-gu, Chonju-si, Chonbuk (KR), 561-330; Soo-Wan Chae, 567-5, Sangsam-ri, Yongjin-myeon, Wanju-gun, Chonbuk (KR), 561-812

(73) Assignees: Jae-Soon Eun, Chonbuk (KR); Yong-Geun Kwak, Chonbuk (KR); Dae-Keun Kim, Chonbuk (KR); Soo-Wan Chae, Chonbuk (KR); Young-Hoon Jung, Seoul (KR); Ok-Pyo Zee, Daejeon (KR)

( * ) Notice: Subject to any disclaimer, the term of this patent is extended or adjusted under 35 U.S.C. 154(b) by 0 days.

(21) Appl. No.: 10/704,940

(22) Filed: Nov. 10, 2003

(65) Prior Publication Data

US 2004/0097533 A1 May 20, 2004

Related U.S. Application Data

(63) Continuation of application No. PCT/KR02/00865, filed on May 9, 2002.

(51) Int. Cl.$^7$ .............................................. A61K 31/44
(52) U.S. Cl. ..................................................... 514/279
(58) Field of Search ......................................... 514/279

(56) References Cited

U.S. PATENT DOCUMENTS 4,737,503 A * 4/1988 Sakamoto et al. .......... 514/279
4,769,452 A * 9/1988 Boulware .................... 540/476

OTHER PUBLICATIONS

Beeton et al. Proceedings of the National Academy of the Sciences of the U.S.A., (Nov. 20, 2001) 98 (24) 13942–7 (ABSTRACT).*
Szewczyk et al. Biochemical pharmacology, (Sep. 1, 2000) 60 (5) 607–14 (ABSTRACT).*
Grahammer et al. Gastroenterology, (May 2001) 120 (6) 1363–71 (ABSTRACT).*
Sanguinetti and Keating "Role of Delayed Rectifier Potassium Channels in Cardiac . . . " *News Physiol. Sci.* 12, 152–157 (1997).
Tristani–Firouzi et al. "Molecular Biology of K$^+$ Channels and Their Role . . . " *Physiology In Medicine* 110, 50–59 (2001).

Fedida et al. "The 1997 Stevenson Award Lecture. Cardiac K$^+$ channel gating: cloned delayed rectifier . . . " *Can. J. Physiol. Pharmacol.* 76, 77–89 (1998).
Grissmer "Potassium channels still hot" TIPS—Oct. 1997 (vol. 18), pp. 347–350.
Wang et al. "Effects of Flecainide, Quinidine, and 4–Aminopyridine on Transient Outward . . . " *J. Pharm. Exp. Thera.* 272, 184–196 (1994).
Kwak et al. "Phosphorylation Is Required for Alteration of Kv1.5 K$^+$ Channel Function by the Kvβ1.3 Subunit" *J. Biol. Chem.* 274, 25355–25361 (1999).
Yang et al. "Inhibition of Cardiac Potassium Currents by the Vesnarinone Analog OPC–18790: Comparison . . . " *J. Pharm. Exper. Ther.* 280, 1170–1175 (1996).
Roden "Mechanism and Management of Proarrhythmia" *Am. J. Cardiol.* 82, 491–571 (1998).
Katz "Selectivity and Toxicity of Antiarrhythmic Drugs: Molecular Interactions . . . " *Am. J. Med.* 104, 179–195 (1998).
Deal et al. "Molecular Physiology of Cardiac Potassium Channels" *Phys. Reviews* 76, 49–67 (1996).
Roden and Tamkun "Toward a Molecular View of Cardiac Arrhythmogenesis . . . " *TCM* 4, 278–285 (1994).
Kwak et al. "KR–30450, a Newly Synthesized Benzopyran Derivative, Activates . . . " *J. Pharm. Exp. Thera.* 275, 807–812 (1995).
Hanaoka et al. "A Novel and Biomimetic Synthesis of (±)–Chelamine . . . " *Chem. Let.* 739–742 (1986).
Snatzke et al. "Absolute Configuration and Chiroptical Properties of Chelidonine . . . " *Tetrahedron* 26, 5013–5028 (1970).
Panzer et al. "Ukraine™, a semisynthetic *Chelidonium majus* alkaloid derivative, acts by . . . " *Cancer Letters* 160 149–157 (2000).
Grynkiewicz et al. "Synthesis and biological activity of O–acyl and O–alkyl chelidonine derivatives" *Eur. J. Med. Chem.* 36, 951–960 (2001).
Panzer et al. "The effects of chelidonoine on tubulin polymerization, cell cycle progression and . . . " *Eur. J. Cell Biol.* 80, 111–118 (2001).
Hiller et al. "Antispasmodic and Relaxant Activity of Chelidonine, Protopine, Coptisine . . . " *Planta Medica* 64, 758–760 (1998).

* cited by examiner

*Primary Examiner*—Raymond J. Henley, III
(74) *Attorney, Agent, or Firm*—Heslin Rothenberg Farley & Mesiti P.C.

(57) ABSTRACT

The present invention relation to a pharmaceutical composition comprising chelidonine or derivatives thereof, with pharmaceutically acceptable carriers. The compositions according to the present invention can selectively block hKv1.5 channels expressed preferentially in human atrial myocytes, and thus are useful as K$^+$ channel blockers and antiarrhythmic drugs.

16 Claims, 12 Drawing Sheets

PHARMACEUTICAL COMPOSITIONS COMPRISING CHELIDONINE OR DERIVATIVES THEREOF

CROSS-REFERENCE TO RELATED APPLICATIONS

This application is a continuation of PCT/KR02/00865 filed May 9, 2002 and published in English as WO 02/092085 on Nov. 21, 2002 and claims priority from KR application No. 2001-25706 filed May 11, 2001, the entire disclosures of which are incorporated herein by reference.

TECHNICAL FIELD

The present invention relates to a composition comprising chelidonine or derivatives thereof, with pharmaceutically acceptable carriers.

BACKGROUND ART

Arrhythmias are abnormal rhythms of the heart and cause the heart to pump less effectively. At this time, electro-biochemical properties on local regions of cardiac muscle are changed due to a variety of causes, and thus abnormal cardiac impulse formation or impulse propagation occurs.

The shape and duration of cardiac action potentials vary depending on the region of the heart where they are recorded. These regional differences result, in part, from the differential expression of $K^+$ channel genes within the myocardium (Sanguinetti and Keating. Role of delayed rectifier potassium channels in cardiac repolarization and arrhythmias. *News Physiol Sci* 1997, 12:152–157).

All antiarrhythmic drugs influence the movement of ions in cardiac muscle to exhibit antiarrhythmic effects. Accordingly, antiarrhythmic drugs are commonly divided into the following classes according to the kinds of the moving ions: I (sodium channel blockers), II (β-adrenergic receptor blockers), III (potassium channel blockers), IV (calcium channel blockers), etc. (Katz A M. Selectivity and toxicity of antiarrhythmic drugs: molecular interactions with ion channels. *AM J Med* 1998, 104: 179–195). A major obstacle to the widespread use of drugs to manage cardiac arrhythmias has been a relatively high incidence of extra-cardiac side effects. With increasingly sophisticated drug development, it is possible to develop drugs that show significantly reduced extracardiac side effects due to the improved tissue-specificity. However, cardiac side effects, which often arise as a direct consequence of drugs' antiarrhythmic mechanisms, have been very difficult to be circumvented. Common cardiac side effects of antiarrhythmic drugs include depressed contractile performance, bradycardia, altered efficacy of pacing and defibrillating devices, and the occurrence of new arrhythmias or increased occurrence of arrhythmias (proarrhythmia) (Roden D M. Mechanism and management of proarrhythmia. *Am J Cardiol* 1998, 82: 491–571).

Antiarrhythmic drugs regulating action potential durations, which are important in controlling heart rate, have already been developed. However, these drugs also produce various side effects as described above, which limits their clinical applications.

Therefore, an ideal antiarrhythmic drug with fewer side effects must act only on cardiac myocytes showing abnormal excitability (or cells having abnormal heart rate), or arrhythmia-occurring tissues (e.g., atrial myocytes, ventricular myocytes, Purkinje fibers, etc). However, drugs satisfying the above requirements have not yet been developed. In order to develop a novel drug with few or no side effects, molecular biological knowledge for the targets of antiarrhythmic drugs (such as ion channels) must be accompanied. For example, the ion channel which selectively expresses in arrhythmogenic tissues, is one of the targets of ideal antiarrhythmic drugs. Accordingly, approaches by the combination of molecular biological cloning techniques and electro-pharmacological techniques will make it possible to develop new ideal antiarrhythmic drugs.

It is well known that various $K^+$ channels regulate action potential durations and $K^+$ channel genes differentially express depending on the regions of the heart. $K^+$ channels represent the most diverse class of ion channels in heart. $K^+$ currents in the myocardium can be classified into two categories: 1) inward $K^+$ currents such as $I_{K1}$ (inward rectifying $K^+$ current), $I_{KAch}$ (acetylcholine-activated $K^+$ current), and $I_{KATP}$ (ATP-sensitive $K^+$ current); and 2) voltage-gated $K^+$ (Kv) currents. The inward $K^+$ currents regulate resting membrane potential, whereas the Kv currents control action potential duration.

The cardiac Kv currents are divided into $I_{to}$, $I_{KP}$, $I_{KR}$, $I_{KUR}$, and $I_{KS}$ in accordance with their electrophysiological characteristics. $I_{to}$ current, a transient outward $K^+$ current, is activated immediately after membrane depolarization, and then becomes inactive rapidly. Therefore, $I_{to}$ is of importance in phase 1 of action potential. $I_{KP}$ current, a plateau $K^+$ current, becomes active only during membrane depolarization, and is a kind of delayed outward $K^+$ current with an intermediate rate of activation. $I_{KR}$ current, a rapidly activating delayed rectifier $K^+$ current, is of importance in phase 2 of action potential. $I_{KUR}$ current, an ultra-rapidly activating delayed rectifier $K^+$ current, is also of importance in phase 2 of action potential. $I_{KS}$ current, a slow-activating delayed rectifier $K^+$ current, takes a few seconds to become active completely, and is of importance in final repolarization of phase 3 of action potential (Roden and George, The cardiac ion channel: relevance to management of arrhythmias. *Annu Rev Med* 1999, 47: 138–148). These Kv channels contribute to cell repolarization and regulate the action potential duration. Clinically, it is known that the repolarization disorders in the damaged tissues result in cardiac arrhythmias. Accordingly, Kv channels become major targets for the treatment of arrhythmias. In practical use, it is known that antiarrhythmic drugs such as quinidine, verapamil, nifedipine, sotalol, amiodarone, flecainide, and cropyrium interact with the Kv channels (Katz A M. Selectivity and toxicity of antiarrhythmic drugs: molecular interactions with ion channels. *Am J Med* 1998, 104: 174–195). However, these drugs are known to have various side effects due to their lack of selectivity for ion channels. Accordingly, there remains a need to develop a novel drug acting specifically on the ion channel in extraordinarily hyperexcitable tissues.

The first cloned $K^+$ channel gene, Shaker, was obtained using the techniques of Drosophila genetics and DNA manipulation. cDNAs of mammalian Kv channel reported until now are divided into nine subfamilies, Kv1~Kv9. Among them, Kv1 subfamily is the most diverse one, and includes at least eight subclasses, Kv1.1~Kv1.8 (Grissner S. Potassium channels still hot, *TiPS* 1997, 18: 347–350). Kv1.1, Kv1.2, Kv1.4, Kv1.5, Kv2.1, Kv4.2 and Kv4.3 of Kv channel genes have been cloned from cardiac tissue (Deal, et al., Molecular physiology of cardiac potassium channels. *Physiol Rev* 1996, 76: 49–67). Main Kv channel genes expressed in human heart are hKv1.4, hKv1.5, hKv4.3 and HERG genes. All these genes are highly expressed in both atrium and ventricle, and in particular, the hKv1.5 gene is preferentially expressed in human atrium. The hKv1.5 is known to have the same electrophysiological and pharmacological properties as $I_{KUR}$, a current specific in human atrium (Fedid, et al., The 1997 Stevenson Award Lecture, Cardiac $K^+$ channel gating: cloned delayed rectifier mechanisms and drug modulation. *Can J Physiol Pharmacol* 1998, 76: 77–89). Development of highly selective blockers for the hKv1.5 channel will lead to an ideal drug for the treatment of atrial fibrillations.

The present inventors have earnestly and intensively searched to develop a selective blocker for the hKv1.5 channel which is preferentially expressed in human atrium, and as a result, have found that chelidonine and derivatives thereof inhibit hKv1.5 channel currents and $I_{KUR}$ currents in human atrial myocytes. In addition, they also found that the prolonging effects of action potential duration are proportional to the heart rate.

Therefore, it is an object of the present invention to provide a composition comprising chelidonine or derivatives thereof which exhibit excellent $K^+$ channel blocking effect and antiarrhythmic effect, with pharmaceutically acceptable carriers.

DISCLOSURE OF THE INVENTION

The present invention relates to a composition comprising chelidonine or derivatives thereof represented by the following formula 1, with pharmaceutically acceptable carriers:

Formula 1

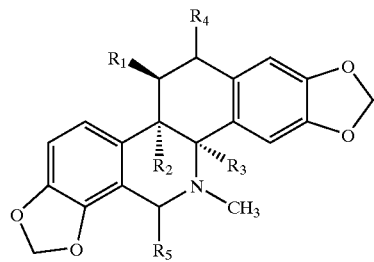

wherein, $R_1$ is selected from the group consisting of hydrogen, hydroxy, a lower alkoxy having 1 to 5 carbon atoms, benzyloxy, a lower alkylcarbonyloxy having 1 to 5 carbon atoms, benzoyloxy, a lower alkylsulfonyloxy having 1 to 5 carbon atoms, arylsulfonyloxy, diphenylphosphonyloxy and —OCONH$_2$;

$R_2$ is hydrogen or methyl; and $R_3$, $R_4$ and $R_5$ are each, independently, hydrogen; or $R_1$ forms a double bond with $R_2$ or $R_4$; or $R_2$ forms a double bond with $R_3$; or $R_5$ forms a double bond with the adjacent N atom.

Preferred compositions according to the present invention comprise chelidonine or derivatives thereof:

wherein, $R_1$ is selected from the group consisting of hydrogen, hydroxy, methoxy, benzyloxy, acetoxy, benzoyloxy, methylsulfonyloxy, 4-methyl-benzenesulfonyloxy, diphenylphosphonyloxy and —OCONH$_2$;

$R_2$ is hydrogen or methyl; and $R_3$, $R_4$ and $R_5$ are each, independently, hydrogen; or $R_1$ forms a double bond with $R_2$ or $R_4$; or $R_2$ forms a double bond with $R_3$; or $R_5$ forms a double bond with the adjacent N atom.

More preferred compositions according to the present invention comprise one selected from the group consisting of:

[5bR-(5bα,6β,12bα)]-5b,6,7,12b,13,14-hexahydro-13-methyl[1,3]benzodioxolo[5,6c]-1,3-dioxolo[4,5-i]phenanthridin-6-ol;

[5bR-(5bα,6β,12bα)]-5b,6,7,12b,13,14-hexahydro-6-methoxy-13-methyl[1,3]-benzodioxolo[5,6c]-1,3-dioxolo[4,5-i]phenanthridine;

[5bR-(5bα,6β,12bα)]-5b,6,7,12b,13,14-hexahydro-6-benzyloxy-13-methyl[1,3]benzodioxolo[5,6c]-1,3-dioxolo[4,5-i]phenanthridine;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-acetate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-benzoate;

(12bR)-13,14-dihydro-13-methyl[1,3]benzodioxolo[5,6c]-1,3-dioxolo[4,5-i]phenanthridine;

(12bR)-7,12b,13,14-tetrahydro-13-methyl[1,3]-benzodioxolo[5,6c]-1,3-dioxolo[4,5-i]phenanthridine;

[5bR-(5bα,6β,12bα)]-5b,6,7,12b,13,14-hexahydro-13-methyl[1,3]benzodioxolo[5,6c]-1,3-dioxolo[4,5-i]phenanthridine;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-diphenylphosphate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-methanesulfonate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-4-methylbenzenesulfonate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-carbamate;

[5bR-(5bα,6β,12bα)]-5b,6,7,12b,13,14-hexahydro-5b,13-dimethyl[1,3]-benzodioxolo[5,6c]-1,3-dioxolo[4,5-i]phenanthridin-6-ol; and 13-methyl[1,3]benzodioxolo[5,6c]-1,3-dioxolo[4,5-i]phenanthridinium.

The structural formulae of the compounds as described above are shown in the following Table 1:

TABLE 1

| Compound No. | Formula | Compound |
|---|---|---|
| 1 | | [5bR-(5bα,6β,12bα)]-5b,6,7,12b,13,14-hexahydro-13-methyl[1,3]benzodioxolo[5,6c]-1,3-dioxolo[4,5-i]phenanthridin-6-ol |

TABLE 1-continued

| Compound No. | Formula | Compound |
|---|---|---|
| 2 | | [5bR-(5bα,6β,12bα)]-5b,6,7,12b,13,14-hexahydro-6-methoxy-13-methyl[1,3]-benzodioxolo[5,6c]-1,3-dioxolo[4,5-i]phenanthridine |
| 3 | | [5bR-(5bα,6β,12bα)]-5b,6,7,12b,13,14-hexahydro-6-benzyloxy-13-methyl[1,3]benzodioxolo[5,6c]-1,3-dioxolo[4,5-i]phenanthridine |
| 4 | | {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-acetate |
| 5 | | {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-benzoate |
| 6 | | (12bR)-13,14-dihydro-13-methyl[1,3]benzodioxolo[5,6c]-1,3-dioxolo[4,5-i]phenanthridine |
| 7 | | (12bR)-7,12b,13,14-tetrahydro-13-methyl[1,3]-benzodioxolo[5,6c]-1,3-dioxolo[4,5-i]phenanthridine |

TABLE 1-continued

| Compound No. | Formula | Compound |
|---|---|---|
| 8 | | [5bR-(5bα,6β,12bα)]-5b,6,7,12b,13,14-hexahydro-13-methyl[1,3]benzodioxolo[5,6c]-1,3-dioxolo[4,5-i]phenanthridine |
| 9 | | {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-diphenylphosphate |
| 10 | | {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-methanesulfonate |
| 11 | | {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-4-methylbenzenesulfonate |
| 12 | | {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-carbamate |
| 13 | | [5bR-(5bα,6β,12bα)]-5b,6,7,12b,13,14-hexahydro-5b,13-dimethyl[1,3]-benzodioxolo[5,6c]-1,3-dioxolo[4,5-i]phenanthridin-6-ol |

TABLE 1-continued

| Compound No. | Formula | Compound |
|---|---|---|
| 14 | | 13-methyl[1,3]benzodioxolo[5,6c]-1,3-dioxolo[4,5-i]phenanthridinium |

Chelidonine of compound 1 used as an effective ingredient in the present is mainly present in plants. Chelidonine has few problems with regard to safety and toxicity. It is well known that chelidonine exhibits anti-spasm effects, inhibitory effects against central dopamine, analgesic effects, antipyretic effects, anti-cancer effects, and inhibitory effects against nitric oxide, corn and verruca.

Compounds 8, 9, 11 and 12 included in the composition of the present invention are novel compounds. On the other hand, compounds other than these compounds have been already disclosed in the literatures below.

Compound 1
Simanek, V. Benzophenanthridine alkaloids. In: The Alkaloids. Academic Press. 1985, Vol. 4, 185–240;

Compound 2
Nowicky, Wassili. Carcinostatic agents and their use. U.S. Pat. No. 1,191,837, 1985, 8, 13, Canada;

Compound 3
Grynkiewicz, Grzegorz; Chojecka-Koryn, Ewa, Gadzikowska, Maria; Chodkowska, Anna, Jagiello-Wojtowicz, Ewa, Synthesis and biological activity of O-acyl and O-alkyl chelidonine derivatives. *Eur J Med Chem.* 2001, 36:951–960;

Compound 4
Grynkiewicz, Grzegorz; Chojecka-Koryn, Ewa, Gadzikowska, Maria; Chodkowska, Anna, Jagiello-Wojtowicz, Ewa, Synthesis and biological activity of O-acyl and O-alkyl chelidonine derivatives. *Eur J Med Chem.* 2001, 36:951–960;

Compound 5
Grynkiewicz, Grzegorz; Chojecka-Koryn, Ewa, Gadzikowska, Maria; Chodkowska, Anna, Jagiello-Wojtowicz, Ewa, Synthesis and biological activity of O-acyl and O-alkyl chelidonine derivatives. *Eur J Med Chem.* 2001, 36:951–960;

Compound 6
Hanaoka, Miyoji; Yoshida, Shuji; Annen, Masami; Mukai, Chisato., A novel and biomimetic synthesis of (±)-chelamine, (±)-chelidonine, sanguinarine, and dihydrosanguinarine from coptisine via a common intermediate. *Chem Lett.* 1986, 5:739–742;

Compound 7
Snatzke, Guenther; Hrbek, Jaroslav, Jr.; Hruben, Ladislav; Horeau, Alain; Santavy, Frantisek, Circular dichroism. XLII. Isolation and chemistry of the alkaloids from some plants of the genus Papaver. L. III. Absolute configuration and chiroptical properties of chelidonine and tetrahydroberberine alkaloids. *Tetrahedron* 1970, 26(21):5013–5028;

Compound 10
Grynkiewicz, Grzegorz; Chojecka-Koryn, Ewa, Gadzikowska, Maria; Chodkowska, Anna, Jagiello-Wojtowicz, Ewa, Synthesis and biological activity of O-acyl and O-alkyl chelidonine derivatives. *Eur J Med Chem.* 2001, 36:951–960;

Compound 13
Takao, Narao A. Alkaloids of Papaveraceae. VI. Alkaloids of Corydalis incisa. 5. The structure of corynoline. *Chem Pharm Bull.* 1963, 11(10):1306–1312;

Compound 14
Lenfield, J. Karoutil, M. Marsalek, E. Slavik, J. Preininger V. and Simanek. V. *J Med Plant Res.* 1981, 43:161–165.

However, no literature teaches or suggests that these chelidonine-based compounds have $K^+$ channel blocking effects and anti-arrhythmic effects.

Chelidonine or derivatives thereof used in the present invention can be either purchased commercially, or prepared by the following methods.

In accordance with the method of Bary, D. K., et al. (The benzophenanthridine alkaloids. *J Nat Prod* 1984, 47:1–43), *Chelidonium majus* var. *asiaticum* is extracted with methanol. Then, the extract is solvent-fractionated with hexane, dichloromethane, butanol and water. Hexane fraction is selected as an active fraction, and purified by silica gel column chromatography (eluent: dichloromethane/ethylacetate/methanol) to prepare chelidonine or its derivatives.

Further, in accordance with the methods of Takeo, et al. (Chiroptische eigenschaften und absolue konfiguration von (+)-14-epicorynolin, (+)-corynolin, (+)-chelidonine und verwandten verbindungen. *Arch Pharm.* (Weinheim) 1984, 317:223–237) and Budabary, et al. (The Merck Index, 8th ed. Merck □Co., 1989, 2038–2039), chelidonine is reacted with RCl (wherein R represents alkyl, phenyl, or phenyl substituted with a halogen or lower alkyl), RCOCl(R represents alkyl, phenyl, or phenyl substituted with a halogen or lower alkyl) and chlorosulfonyl isocyanate to prepare chelidonine or its derivatives.

Some compounds used in the present invention can also be prepared in accordance with the following reaction schemes 1 to 5. These schemes are only illustrative of preferred methods for preparing compounds used in the present invention. These schemes, however, are not to be construed as limiting the scope of the present invention.

Scheme 1

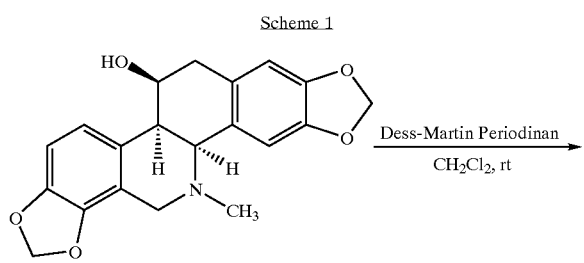

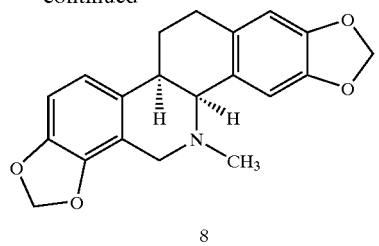

By treating chelidonine with Dess-Martin Periodinane oxidizing agent, the secondary alcohol is subjected to dehydration and oxidation to prepare a compound 6.

Scheme 2

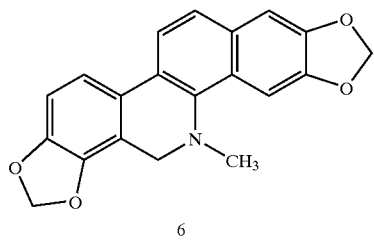

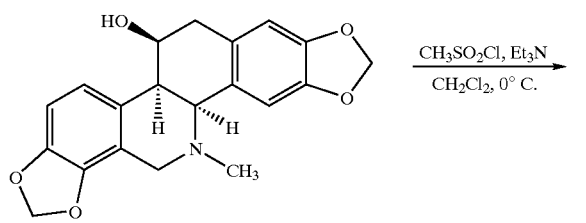

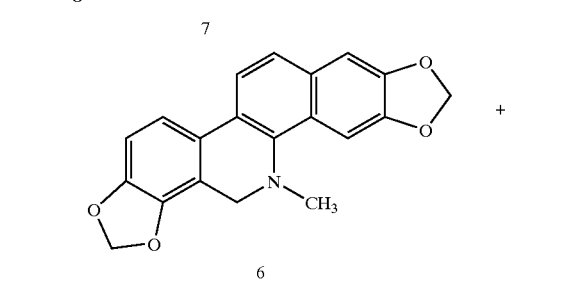

Chelidonine is treated with methanesulfonyl chloride in the presence of triethylamine to obtain a mesylate compound 10. The compound 10 thus obtained is subjected to elimination reaction with potassium t-butoxide to obtain a compound 7. A double bond present in the compound 7 is reduced with hydrogen in the presence of palladium catalyst to prepare a mixture of compounds 6 and 8.

Scheme 3

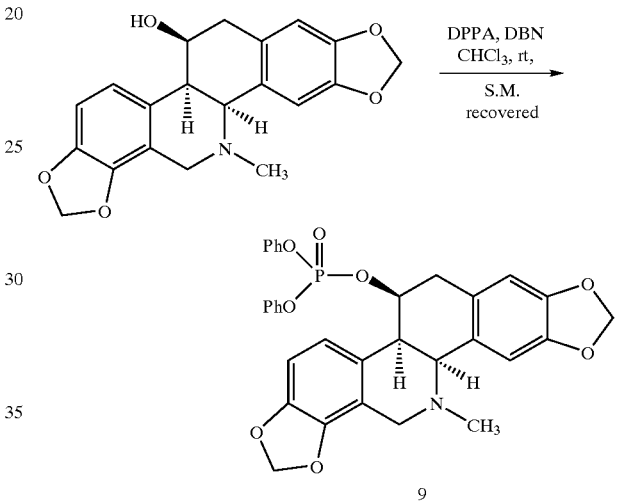

Chelidonine is treated with diphenylphosphoryl azide in the presence of 1,5-diazabicyclo[4,3,0]non-5-ene as a base to prepare a phosphoric acid ester compound 9. At this time, the starting material is recovered from the reaction.

Scheme 4

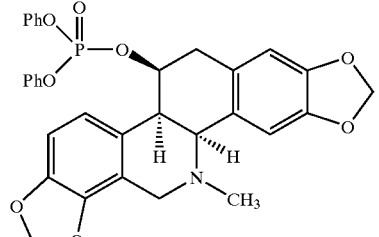

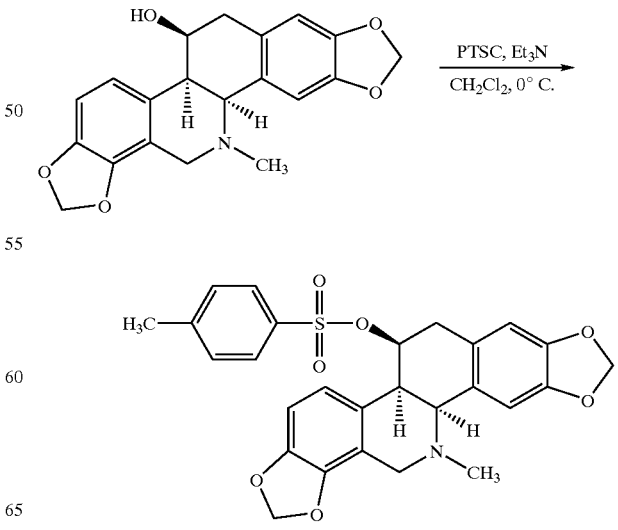

Chelidonine is treated with para-toluenesulfonyl chloride in the presence of triethylamine as a base to prepare a sulfone ester compound 11.

Scheme 5

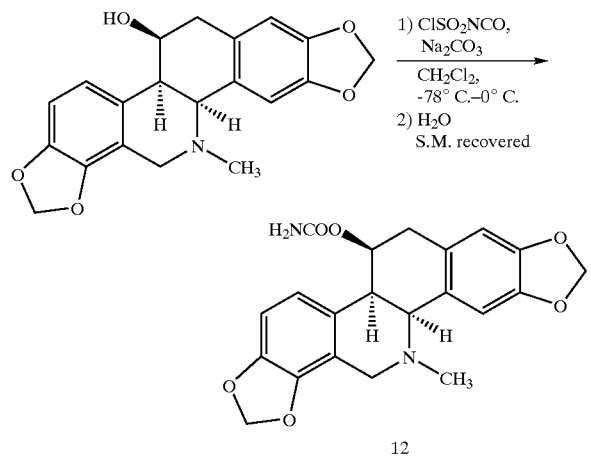

Chelidonine is treated with chlorosulfonyl isocyanate in the presence of sodium carbonate as a base, and then hydrolyzed to prepare a carbamate compound 12. The starting material is recovered from the reaction.

Examples of pharmaceutically acceptable carriers which may be included in the compositions according to the present invention include excipients, binding agents, lubricants, disintegrating agents, coating agents, emulsifying agents, suspending agents, solvents, stabilizers, absorption agents, water for injection, isotonic agents, etc. The compositions according to the present invention can include at least one selected from these carriers.

The compositions of the present invention can be used as formulations for oral administration or injection, and formulations for oral administration are preferred. Formulations for oral administration can be in the form of granules, tablets, capsules, solutions, etc.

The dosage for the compositions of the present invention can be varied depending upon known factors, such as age, sex, and weight of the patient. The daily dosage is commonly in the range of 10 to 5000 mg, and preferably 50 to 1000 mg.

The toxicity of chelidonine is 34.6±2.44 mg/kg when administered to a mouse intravenously, and that of sanguinarine (compound 14) is 15.9 mg/kg when administered to a mouse intravenously and 102.0 mg/kg when administered subcutaneously.

The compositions of the present invention can be used as $K^+$ channel blocking agents and anti-arrhythmic agents, and also used for the treatment of warm-blooded animals such as mouse, dog, rabbit, cat, domestic fowl, etc,.

BEST MODE FOR CARRYING OUT THE INVENTION

Figure 1A:
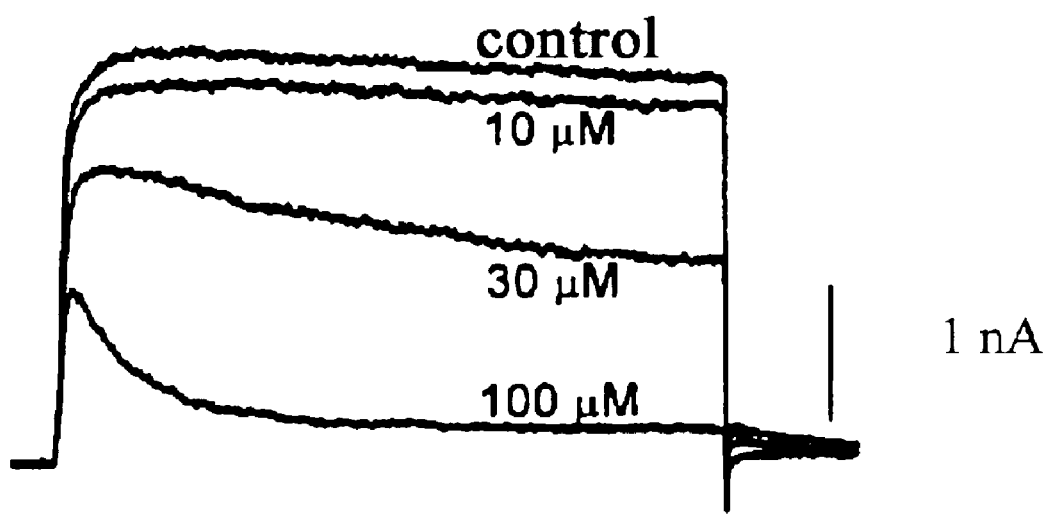
FIG. 1a shows the effect of chelidonine (compound 1) on the hKv1.5 currents expressed in Ltk-cells. The current traces were recorded with a depolarizing pulse of +50 mV from a holding potential of −80 mV.
Figure 1B:
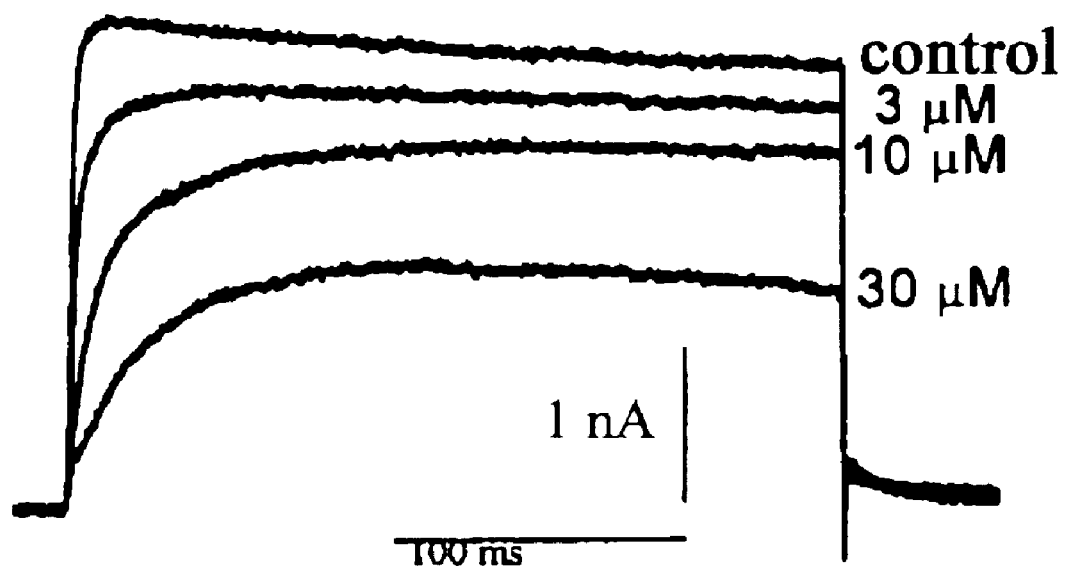
FIG. 1b shows the effect of sanguinarine (compound 14) on the hKv1.5 currents expressed in Ltk-cells. The current traces recorded with depolarizing step to +50 mV from a holding potential of −80 mV in the absence and the presence of various concentrations of sanguinarine.
Figure 1C:
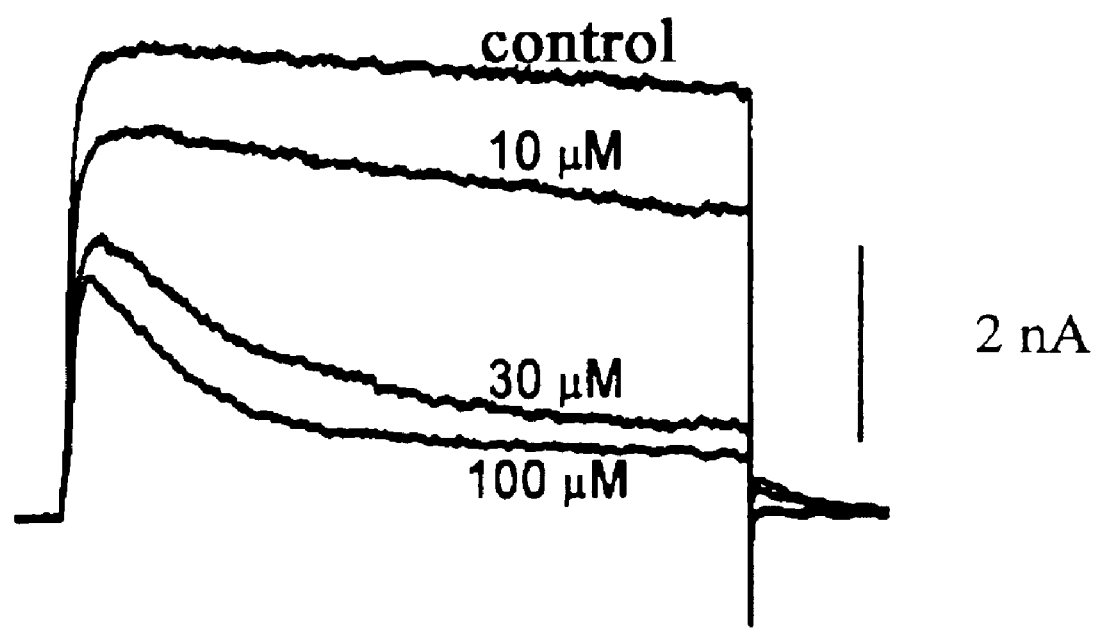
FIG. 1c shows the effect of acetylchelidonine (compound 4) on the hKv1.5 currents expressed in Ltk-cells. The current traces recorded with depolarizing step to +50 mV from a holding potential of −80 mV in the absence and the presence of various concentrations of acetylchelidonine.
Figure 1D:
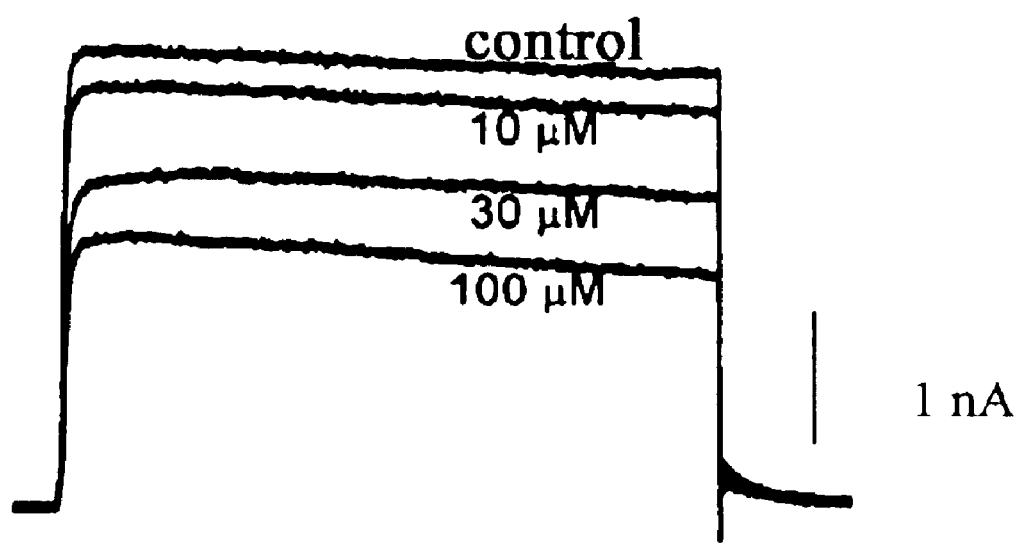
FIG. 1d shows the effect of benzoylchelidonine (compound 5) on the hKv11.5 currents expressed in Ltk-cells. The current traces recorded with depolarizing step to +50 mV from a holding potential of −80 mV in the absence and the presence of various concentrations of benzoylchelidonine.

The present invention will now be described in more detail with reference to the following examples. However, these examples are given by way of illustration and not of limitation.

EXAMPLE 1

Preparation of (12bR)-13,14-dihydro-13-methyl[1,3]benzodioxolo[5,6c]-1,3-dioxolo[4,5-i]phenanthridine (Compound 6)

Dess-Martin Periodinane (25 mg, 0.059 mmol) was dissolved in anhydrous methylene dichloride (0.2 ml), and then stirred at room temperature for 10 minutes. A solution of chelidonine (20 mg, 0.054 mmol) in anhydrous methylene dichloride 0.1 ml) was added dropwise to the reaction solution. After stirring for 30 minutes, diethyl ether (0.9 ml) was added to the reaction solution. The reaction solution was added to a mixture of saturated aqueous potassium carbonate solution (0.56 ml) and sodium thiosulfate pentahydrate (0.1 g) and then stirred for 15 minutes. The reaction solution was extracted with ethylacetate, washed, dried, and purified by column chromatography (hexane:ethylacetate=10:1) to prepare 6.6 mg (37%) of the title compound (compound 6). At this time, 9 mg (45%) of chelidonine was recovered.

$R_f$=0.24 (hexane:ethylacetate=10:1)

$^1$H-NMR (500 MHz, CDCl$_3$): δ7.71 (d, 1H, J=9.0 Hz), 7.60 (d, 1H, J=14 Hz), 7.50 (d, 1H, J=8.5 Hz), 7.32 (d, 1H, J=8.0 Hz), 7.27 (s, 1H), 6.87 (d, 1H, J=8.5 Hz), 6.07 (s, 2H), 6.06 (s, 2H), 4.21 (s, 2H), 2.64 (s, 3H).

EXAMPLE 2

Preparation of (12bR)-7,12b,13,14-tetrahydro-13-methyl[1,3]-benzodioxolo[5,6c]-1,3-dioxolo[4,5-i]phenanthridine (Compound 7)

A solution of the compound 10 (20 mg, 0.046 mmol) in anhydrous methanol (0.3 ml) was stirred at room temperature for 10 minutes, and then potassium t-butoxide (15 mg, 0.138 mmol) was added thereto. The reaction solution was stirred at room temperature for 13 hours. The reaction solution was extracted with ethylacetate, washed, dried, and purified by column chromatography (hexane:ethylacetate= 4:1) to prepare 10 mg (64%) of the title compound (compound 7).

$R_f$=0.22 (hexane:ethylacetate=4:1)

$^1$H-NMR (500 MHz, CDCl$_3$): δ 7.16 (d, 1H, J=6.0 Hz), 7.16 (d, 1H, J=8.0 Hz), 6.74 (d, 1H, J=8.0 Hz), 6.60 (s, 1H), 6.50–6.48 (m, 1H), 5.97 (d, 2H, J=10 Hz), 5.93 (d, 2H, J=10 Hz), 4.56–4.53 (m, 1H), 4.43 (d, 2H, J=16.5 Hz), 3.92 (d, 2H, J=16.5 Hz), 3.59–3.41 (m, 2H), 1.99 (s, 3H).

EXAMPLE 3

Preparation of [5bR-(5bα,6β,12bα)]-5b,6,7,12b,13,14-hexahydro-13-methyl[1,3]benzodioxolo[5,6c]-i1,3-dioxolo[4,5-i]phenanthridine (Compound 8)

10% palladium (1 mg) was added to the compound 7 (10 mg, 0.030 mmol) in anhydrous methanol (0.3 ml) and stirred at room temperature for 10 minutes. While feeding with hydrogen, the reaction solution was stirred for 1 hour. The reaction solution was filtered through a pad of celite, concentrated under reduced pressure, and purified by column chromatography (hexane:ethylacetate=6: 1) to prepare a mixture of 2 mg (20%) of the title compound 8 and 1.8 mg (18%) of the compound 6.

$R_f$=0.27 (hexane:ethylacetate=6:1)

$^1$H-NMR (500 MHz, CDCl$_3$): δ 6.93 (s, 1H), 6.75 (d, 1H, J=8.5 Hz), 6.72 (d, 1H, J=8.5 Hz), 6.56 (s, 1H), 5.94 (d, 2H, J=15 Hz), 5.92 (d, 2H, J=3 Hz), 3.94 (d, 1H, J=16.5 Hz), 3.61 (d, 1H, J=4.0 Hz), 3.48 (d, 1H, J=16 Hz), 3.07–3.04 (m, 1H), 2.79–2.67 (m, 2H), 2.40 (s, 3H), 1.91–1.88 (m, 1H).

EXAMPLE 4

Preparation of {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-diphenylphosphate (Compound 9)

1,5-diazabicyclo[4,3,0]non-5-yne (30 μl, 0.243 mmol) was added to the solution of chelidonine (30 mg, 0.081 mmol) in anhydrous chloroform (0.4 ml) and stirred at room temperature for 30 minutes. Diphenylphosphoryl azide (27 μl, 0.122 mmol) was added to the solution, and stirred for 12 hours. The resulting reaction solution was extracted with ethylacetate, washed, dried, and purified by column chromatography (hexane:ethylacetate=2:1) to prepare 20 mg (42%) of the title compound (compound 9). At this time, 11 mg (37%) of chelidonine was recovered.

$R_f$=0.31 (hexane:ethylacetate=2:1)

$^1$H-NMR (500 MHz, CDCl$_3$): δ 7.41–7.35 (m, 5H), 7.31–7.19 (m, 7H), 6.59 (d, 1H, J=8.5 Hz), 6.37 (s, 1H), 5.90 (s, 2H), 5.88 (d, 2H, J=23 Hz), 5.11–5.05 (m, 1H), 4.10 (d, 2H, J=5.0 Hz), 3.70 (d, 2H, J=17.5 Hz), 3.66 (bs, 1H), 3.44 (d, 2H, J=17 Hz),2.99 (1H, dd, J=11, 15 Hz),2.87(1H, dd, J=5, 15.5 Hz),2.53 (s, 3H).

EXAMPLE 5

Preparation of {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-methanesulfonate (compound 10)

Chelidonine (18 mg, 0.048 mmol) was dissolved in anhydrous methylene dichloride (0.5 ml), and then stirred at 0° C. for 10 minutes. Anhydrous triethylamine (8 μl, 0.058 mmol) and methanesulfonyl chloride (6 μl, 0.073 mmol) were added to the solution, and stirred at room temperature for 6 hours. The resulting reaction solution was extracted with ethylacetate, washed, dried, and purified by column chromatography (hexane:ethylacetate=2:1) to prepare 16 mg (77%) of the title compound (compound 10).

$R_f$=0.39 (hexane:ethylacetate=2:1)

$^1$H-NMR (500 MHz, CDCl$_3$): δ 7.21 (d, 1H, J=8.0 Hz), 7.18 (s, 1H), 6.69 (d, 1H, J=8.5 Hz), 6.42 (s, 1H), 5.90 (d, 2H, J=5.0 Hz), 5.88 (d, 2H, J=15.5 Hz), 5.18–5.16 (m, 1H), 4.13–4.11 (m, 1H), 3.75 (s, 1H), 3.73 (d, 2H, J=12 Hz), 3.45 (d, 2H, J=17 Hz), 3.14–3.08 (m, 1H), 3.05 (s, 3H), 2.94 (1H, dd, J=5.0, 15 Hz), 2.54 (s, 3H).

EXAMPLE 6

Preparation of {[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-4-methylbenzenesulfonate (Compound 11)

A solution of chelidonine (10 mg, 0.027 mmol) in anhydrous methylene dichloride (0.3 ml) was stirred at 0° C. for 10 minutes. Anhydrous triethylamine (5 μl, 0.032 mmol) and paratoluenesulfonyl chloride (8 μl, 0.040 mmol) were added to the solution, and stirred at room temperature for 12 hours. The resulting reaction solution was extracted with ethylacetate, washed, dried, and purified by column chromatography (hexane:ethylacetate=2:1) to prepared 8.6 mg (63%) of the title compound (compound 11).

$R_f$=0.36 (hexane:ethylacetate=2:1)

$^1$H-NMR (500 MHz, CDCl$_3$): δ 7.86 (d, 2H, J=8.5 Hz), 7.37 (d, 2H, J=8.5 Hz), 7.30–7.26 (m, 1H), 7.20 (s, 1H), 6.66 (d, 2H, J=8.0 Hz), 6.33 (s, 1H), 5.89 (d, 2H, J=3.5 Hz), 5.87 (d, 2H, J=18 Hz), 4.96–4.92 (m, 1H), 4.03 (d, 1H, J=5.0 Hz), 3.67 (d, 2H, J=17.5 Hz), 3.60 (bs, 1H), 3.42 (d, 2H, J=17.5 Hz), 2.98 (1H, dd, J=11.5, 15 Hz), 2.68 (1H, dd, J=5.0, 15.5 Hz), 2.51 (s, 3H), 2.47 (s, 3H).

EXAMPLE 7

Preparation of {[5bR-(5bα,6β,12bα)]-5b,6,7,12b,13,14-hexahydro-13-[1,3]benzodioxolo[5,6c]-1,3-dioxolo[4,5-i]phenanthridin-6-yl}-carbamate (Compound 12)

A solution of sodium carbonate (10 mg, 0.097 mmol) and chlorosulfonyl isocyanate (6 μl, 0.065 mmol) in anhydrous methylene dichloride (0.4 ml) was stirred at −78° C. for 10 minutes. A solution of chelidonine (20 mg, 0.054 mmol) in anhydrous methylene dichloride (0.14 ml) was added dropwise to the reaction solution. After the resulting reaction solution was stirred for 1 hour and slowly heated to 0° C., the reaction was quenched with water. The reaction solution was brought to pH >7 with 3N aqueous sodium hydroxide solution. Subsequently, the reaction solution was extracted with ethylacetate, washed, dried and purified by column chromatography (hexane:ethylacetate=1:1) to prepare 5.4 mg (20%) of the title compound (compound 12). At this time, 4 mg (40%) of chelidonine was recovered.

$R_f$=0.31 (hexane:ethylacetate=1:1)

$^1$H-NMR (500 MHz, CDCl$_3$): δ 7.26 (d, 1H, J=8.5 Hz), 7.21 (s, 1H), 6.71 (d, 1H, J=8.5 Hz), 6.45 (s, 1H), 5.92 (d, 2H, J=5.5 Hz), 5.90 (d, 2H, J=14.5 Hz), 5.11–5.07 (m, 1H), 4.78 (bs, 2H), 4.15 (bs, 1H), 3.83 (bs, 1H), 3.75–3.80 (m, 1H), 3.50–3.43 (m, 1H), 3.09–3.08 (m, 1H), 3.02 (dd, 1H, J=5.0, 15 Hz), 2.59 (s, 3H).

EXPERIMENTAL EXAMPLE 1

Effects of Chelidonine and Derivatives thereof on hKv1.5 Channel Currents

Preparation of Cell Line Expressing a Specific Ion Channel

Cell line selectively expressing a specific cardiac K$^+$ channel gene was prepared according to the method described in the thesis (Yang, et al., Inhibition of cardiac potassium currents by the vesnarinone analog OPC-18790: comparison with quinidine and dofetilide. *J Pharmacol Exp Ther.* 1997, 280: 1170–1175; Kwak, et al., Phosphorylation is required for alteration of Kv1.5 K$^+$ channel function by the Kvbeta 1.3 subunit. *J Biol Chem* 1999, 274: 25355–25361).

First, cDNAs for human cardiac K$^+$ channel genes such as hKv 1.5 and HERG were subcloned into pMSVneo which contain dexamethasone-inducible murine mammary tumor virus promoter controlling transcription of the inserted cDNA and a gene conferring neomycin resistance driven by the SV40 early promotor. The cDNA-containing expression vector was transfected into mouse Ltk-cells with lipofectamine. After 24 hours, the cells selection with 0.5 µg/ml of G418 was performed for 2 weeks or until discrete foci formed. Individual foci were isolated, maintained in 0.25 µg/ml of G418, and screened by Norhtern analysis and electrophysiological analysis. Transfected cells were cultured in Dulbeco's modified Eagle medium (DMEM) supplemented with 10% horse serum and 0.25 µg/ml of G418, under 5% CO$_2$. Transiently transfected cells were cultured in DMEM media supplemented with only 10% horse serum, differently from stable cell lines.

2) Electrical Recording

Currents in human atrial myocytes and cell lines were recorded by using the whole cell configuration of the gigaohm-seal patch clamp techniques (Kwak, et al., Phosphorylation is required for alteration of Kv1.5 K$^+$ channel function by the Kvbeta 1.3 subunit. *J Biol Chem* 1999, 274: 25355–25361). First, electrical signals were amplified with a patch clamp amplifier (Axon Instruments, Axopatch-1D, Foster, USA). Currents were digitized by a signal converter (Digidata 1200, Axon Instruments) and stored on the hard disk of a computer. The micropipette with a resistance of 1~2MΩ (Kimax-51, 1.5=14 1.8×10 mm) for current recording, was pulled out by a 2-stage pipette puller (Narishige, PP-83). The intracellular pipette-filling solution for whole cell mode contained 100 mM KCl, 10 mM HEPES, 5 mM K$_4$BAPTA, 5 mM K$_2$ATP and 1 mM MgCl$_2$ (pH 7.2). The extracellular solution contained 130 mM NaCl, 4 mM KCl, 1.8 mM CaCl$_2$, 1 mM MgCl$_2$, 10 mM HEPES and 10 mM glucose (pH 7.35).

Figure 1E:
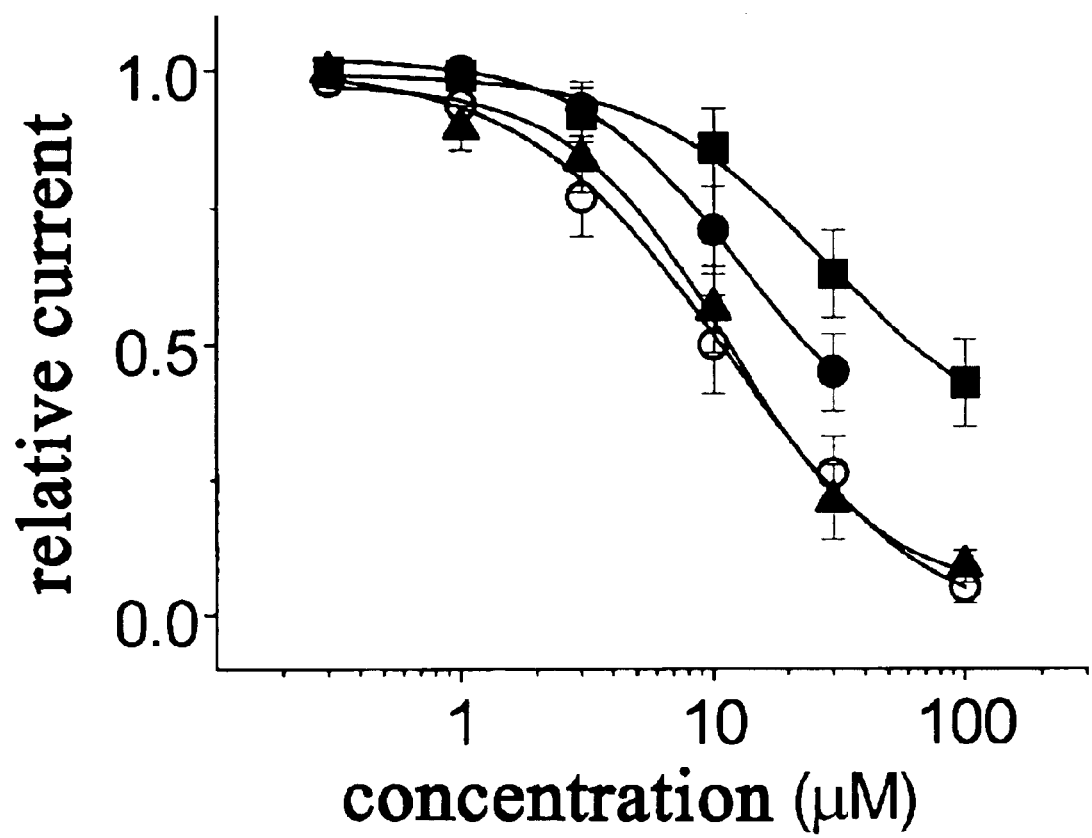
FIG. 1e is concentration-response relationships of hKv1.5 block by chelidonine (compound 1, ○), acetylchelidonine (compound 4, ▲), benzoylchelidonine (compound 5, ■), and sanguinarine (compound 14, ●), respectively. Steady state currents taken at the end of the depolarizing pulse were normalized to control to construct the concentration-response curve.

The current traces were recorded with a depolarizing pulse of +50 mV from a holding potential of −80 mV, followed by a repolarizing pulse of −50 mV in the Ltk-cells. To observe the concentration-dependent block of hKv1.5 channel currents by each compound, steady-state currents taken at the end of the depolarizing pulse of +50 mV were normalized to the control obtained in the absence of each compound FIGS. 1a to 1d show the concentration-dependent inhibitory effects of chelidonine (compound 1), sanguinarine (compound 14), acetylchelidonine (compound 4) and benzoylchelidonine (compound 5) on the hKv1.5 channel currents expressed in the Ltk-cells. FIG. 1e is concentration-response curves showing the relative steady-state currents obtained at the end of the depolarizing pulse against the concentration of each compound. Data were fitted with a Hill equation.

FIGS. 1a to 1e confirmed that these compounds exhibit concentration-dependent inhibitory effects on the hKv1.5 channel currents expressed in Ltk-cells, and that the inhibitory effects varied somewhat depending on the types of derivatives. Especially, chelidonine (compound 1) and acetylchelidonine (compound 4) predominantly blocked the open ion channels. In contrast, sanguinarine (compound 14) slowed the channel activation, and benzoylchelidonine (compound 5) showed the tonic blocking effects.

IC$_{50}$ values (50% inhibitory concentration, µM) of compounds 1~14 on the hKv1.5 channel currents were determined, and Hill values were calculated from the concentration-response curves of the respective compounds using the Hill equation. These results are listed in Table 2.

TABLE 2

| IC$_{50}$ and Hill values of chelidonine and derivatives thereof | | |
|---|---|---|
| Compound | IC$_{50}$(µM) | Hill value |
| Compound 1 | 11.5 ± 3.1 | 1.07 |
| Compound 2 | 45.2 ± 4.1 | 1.29 |
| Compound 3 | 59.3 ± 3.0 | 1.37 |
| Compound 4 | 11.3 ± 3.3 | 1.34 |
| Compound 5 | 29.3 ± 4.2 | 1.18 |
| Compound 6 | 26.4 ± 3.9 | 1.09 |
| Compound 7 | 19.9 ± 3.5 | 0.98 |
| Compound 8 | 65.6 ± 4.2 | 1.38 |
| Compound 9 | 48.6 ± 3.5 | 1.26 |
| Compound 10 | 31.3 ± 3.5 | 1.20 |
| Compound 11 | 29.6 ± 3.7 | 1.19 |
| Compound 12 | 1.9 ± 1.0 | 1.12 |
| Compound 13 | 27.5 ± 3.7 | 1.34 |
| Compound 14 | 13.0 ± 3.8 | 1.39 |

EXPERIMENTAL EXAMPLE 2

Voltage-dependent Block of hKv1.5 Channel Currents Expressed in Ltk-cells by Chelidonine Voltage-dependence of the drugs acting on ion channels is sometimes very useful in evaluating the clinical applications of the drugs.

Figure 2:
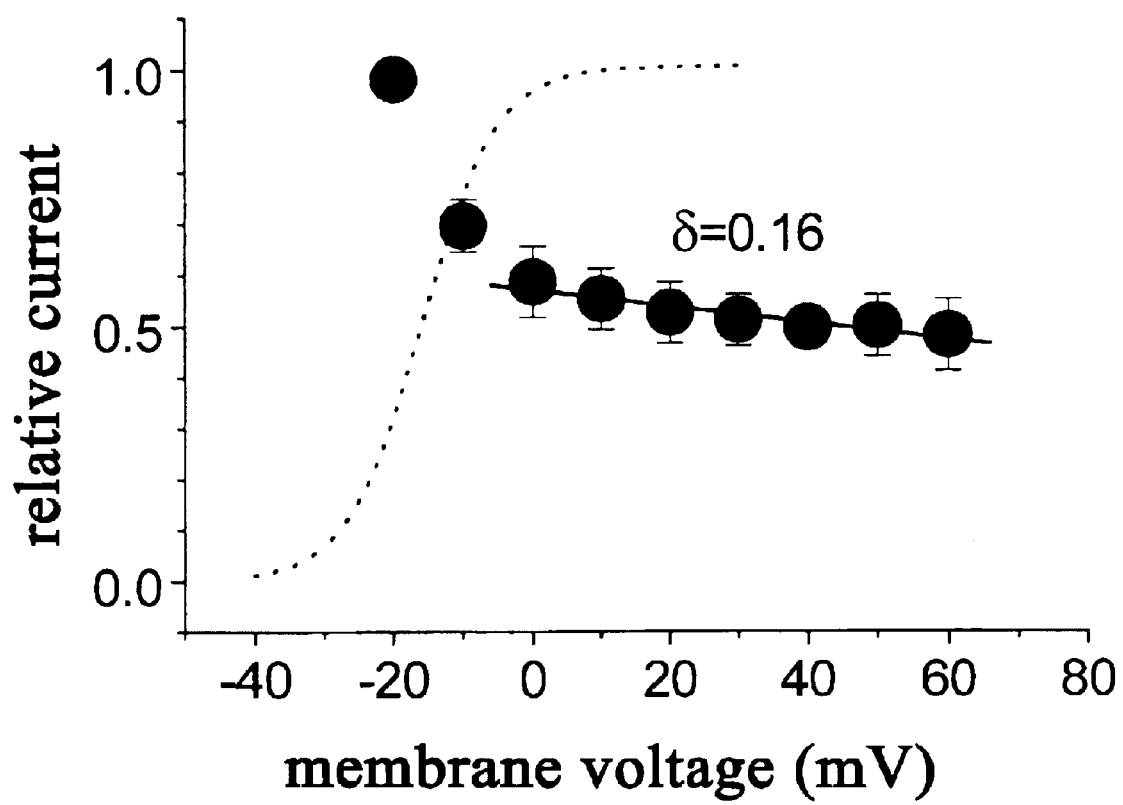
FIG. 2 shows the voltage-dependent block of hKv1.5 expressed in Ltk-cells by chelidonine (compound 1, 10 μM)

To quantify the voltage-dependent block of chelidonine (compound 1), the relative steady state current, I$_{chelidonine}$/I$_{control}$ was plotted as a function of membrane potential (FIG. 2). The steady-state currents were obtained at the end stage of 250 ms depolarizing pulses, while increasing the membrane voltage by 10 mV from −80 to +60 mV. The dotted line denotes the activation curve of hKv1.5 channel current expressed in Ltk-cells.

As shown in FIG. 2, chelidonine (compound 1) showed a strong voltage-dependence between −30 mV and 0 mV, but a weak voltage-dependence between 0 mV and +60 mV. δ values between 0 mV and +60 mV are 0.16±0.01 (n=7) when calculated using the Woodhull equation.

EXPERIMENTAL EXAMPLE 3

Channel State-dependency of hKv1.5 Block by Chelidonine

Figure 3:
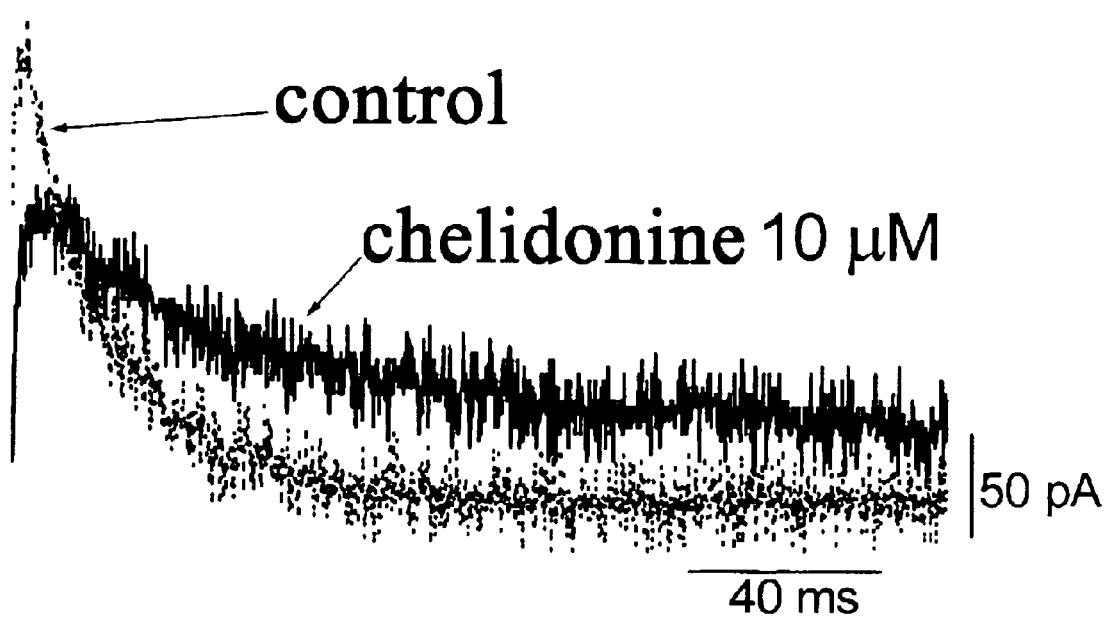
FIG. 3 shows the channel state-dependent block of hKv1.5 expressed in Ltk-cells by chelidonine (compound 1, 10 μM)

We tested the channel state-dependency of hKv1.5 block by chelidonine (FIG. 3).

FIG. 3 shows the superposition of the tail currents obtained with a depolarizing pulse of +50 mV from a holding potential of −80 mV, followed by a repolarizing pulse of −50 mV under control conditions and in the presence of chelidonine (10 μM).

Under control conditions, the tail currents were rapidly deactivated. In the presence of chelidonine, the initial amplitude of the tail current was reduced, but the subsequent decline of the tail current was slower than that under control conditions, which resulted in a "crossover" phenomenon. This suggests that chelidonine acts as an open channel blocker on the hKv1.5 channel. That is, chelidonine exhibited stronger inhibitory effects on the hKv1.5 channel in an open state than that in a closed state.

EXPERIMENTAL EXAMPLE 4

Effects of Chelidonine on the $K^+$ Current in Human Atrial Myocyte

Isolation of human atrial myocytes was carried out by the Wang, et al.'s method (Effects of flecainide, quinidine, and 4-aminopyridine on transient outward and ultrarapid delayed rectifier currents in human atrial myocytes. J Pharmacol Exp Ther 1995, 272: 184–196). Specimens of human right atrial appendage were obtained from the hearts of patients undergoing cardiopulmonary bypass surgery. The procedure for obtaining the tissue was approved by the patient. Samples obtained were quickly immersed in $Ca^{2+}$-free Krebs Henseleit (KH) solution. The myocardial specimen was chopped and placed in a triangular flask containing 10 ml of the $Ca^{2+}$-free KH solution, followed by agitation for 5 minutes. After removing the supernatant, the tissue was resuspended in 10 ml solution containing 200 U/ml collagenase and 4 U/ml protease and incubated for 45 min. After removing the supernatant, the tissue was resuspended in a 10 ml enzyme-containing solution (in a triangular flask). In order to determine the number and quality of the isolated cells, the medium was examined every 15 min under an inverted microscope. The tissue was incubated until the yield seemed to be maximal. After the incubation, the tissue was transferred to a storing solution. Cells were separated with a pipette, and centrifuged for 5 min under 250 g. The sediment was resuspended in a storing solution [composition: 20 mM KCl, 10 mM $KH_2PO_4$, 10 mM glucose, 70 mM glutamic acid, 10 mM β-hydroxybutyric acid, 10 mM taurine, 10 mM EGTA and 0.1% albumin, pH was adjusted to 7.4 with KOH and stored for current recording.

Figure 4A:
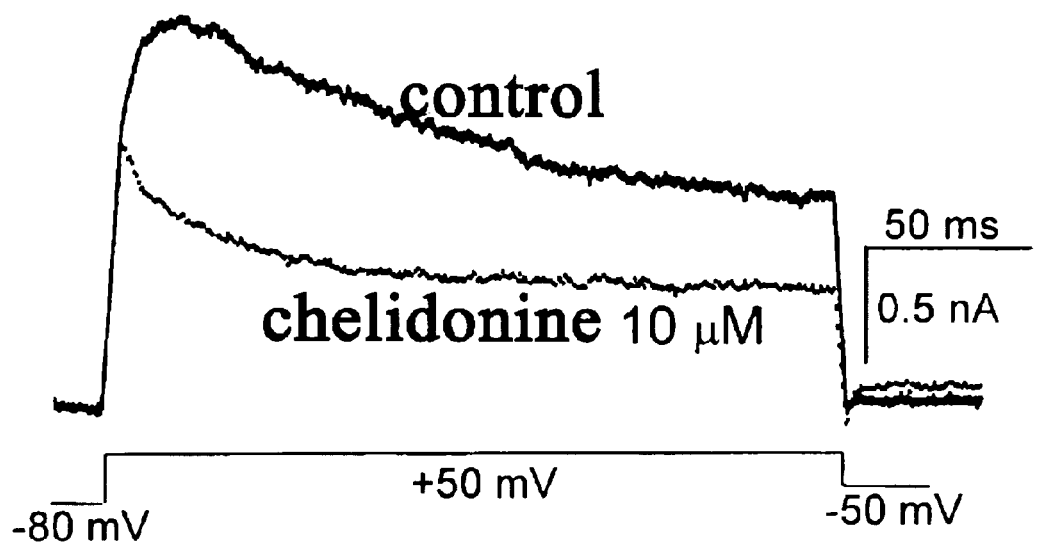
FIG. 4a shows representative $K^+$ current tracings for the effect of chelidonine (compound 1, 10 μM) on the $K^+$ channel current in human atrial myocytes. $K^+$ currents were obtained by depolarizing pulse of +50 mV from a holding potential of −80 mV.
Figure 4B:
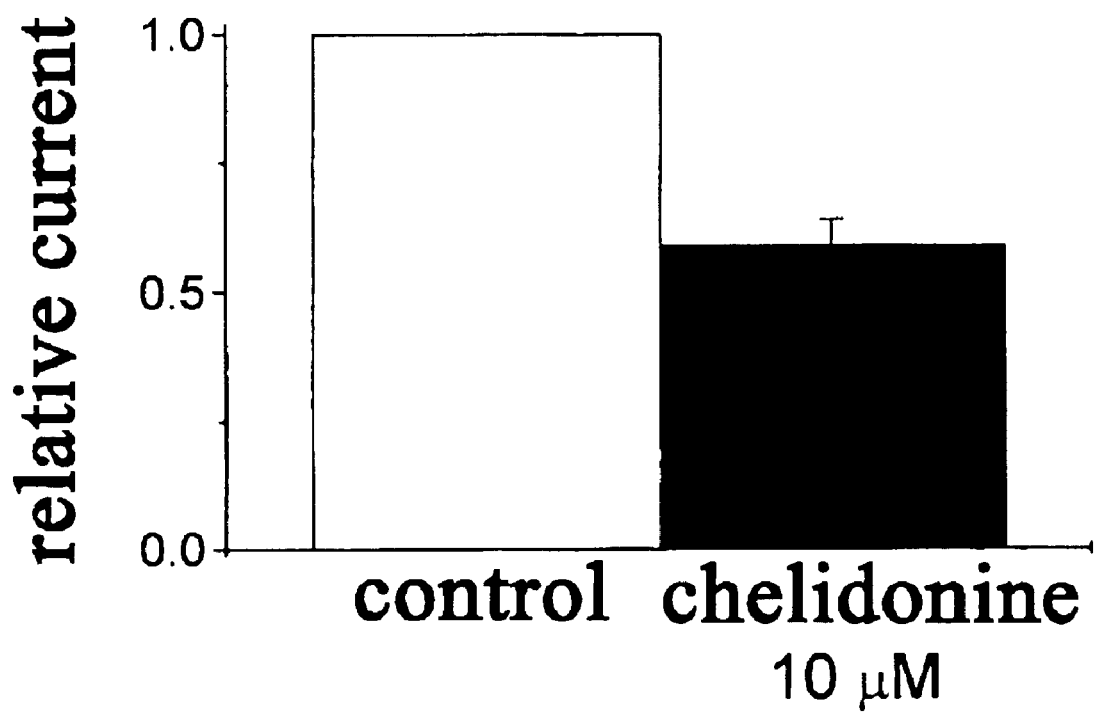
FIG. 4b shows the averaged currents obtained in FIG. 4a as determined at the end of the pulse in seven cells.

We investigated whether inhibitory effect on the hKv1.5 channel currents by chelidonine is similarly shown for $K^+$ channel currents of human atrial myocytes, which has been known to express hKv1.5 channel highly. Human atrial myocytes were isolated from the hearts of patients without any type of arrhythmia undergoing cardiopulmonary bypass surgery. FIG. 4a shows the current traces evoked by depolarizing pulse of +50 mV from a holding potential of −80 mV, then repolarizing to −50 mV. FIG. 4b denotes the averaged steady state currents obtained at the end stage of a depolarizing pulse.

The outward rectifying $K^+$ currents in human atrial myocytes consist of the rapidly activating and rapidly inactivating current and the delayed rectifying current, as shown in FIG. 4a. Chelidonine (compound 1, 10 μM) decreased the peak amplitude of outward $K^+$ current in human atrial myocytes and accelerated inactivation process, resulting in the decrease of the steady state current. FIG. 4b shows that 10 μM chelidonine inhibits the steady-state currents at the end of the depolarizing pulse of +50 mV by 41±5% (n=7), compared to the control. Therefore, it was confirmed that inhibitory effect of chelidonine on the hKv 1.5 expressed in Ltk-cells is also shown in human atrial myocytes.

EXPERIMENTAL EXAMPLE 5

Frequency-dependent Effects of Chelidonine and Derivatives thereof on Action Potentials of Rabbit Atrial Tissue Action potentials in rabbit atrial tissue were recorded according to the method described in thesis by Kwak, et al. (A newly synthesized benzopyran derivatives, activates the cardiac ATP-sensitive $K^+$ channel. J Pharmacol Exp Ther 1995, 275: 807–812).

Male New Zealand white rabbits weighing about 2 kg were stunned with a blow on the head and hearts were rapidly excised and transferred to a dissection bath filled with Tyrode's solution saturated with 97% $O_2$ and 3% $CO_2$ gas mixture and each dissected tissue was mounted horizontally in a narrow channel of a tissue chamber and continuously superfused with the Tyrode's solution at 37° C. The action potentials were elicited by stimulating the cardiac cells with square pulses (1~5 Hz, 1-ms duration, 20–30% above threshold voltage) by a stimulator. Action potentials were recorded with a 3 M KCl-filled microelectrode (10–20 megaohm) connected to an amplifier (KS-700, WPI, Sarasota, Fla., USA), and were displayed on an oscilloscope (Dual beam storage 5113, Tektronix, Beaverton, Oreg., USA). Tracings on the oscilloscope screen were photographed on a 35-mm film and also recorded on a physiograph (RS 3400, Gould, Cleveland, Ohio). $APD_{90}$ was used for the comparison of action potential durations. $APD_{90}$ represents the action potential duration at 90% repolarization, relative to the action potential duration at maximum 100% depolarization. Images on the oscilloscope screen were captured on Polaroid camera.

We tested whether the effect of chelidonine on action potentials of rabbit atrial myocytes are frequency-dependent or not.

Figure 5A:
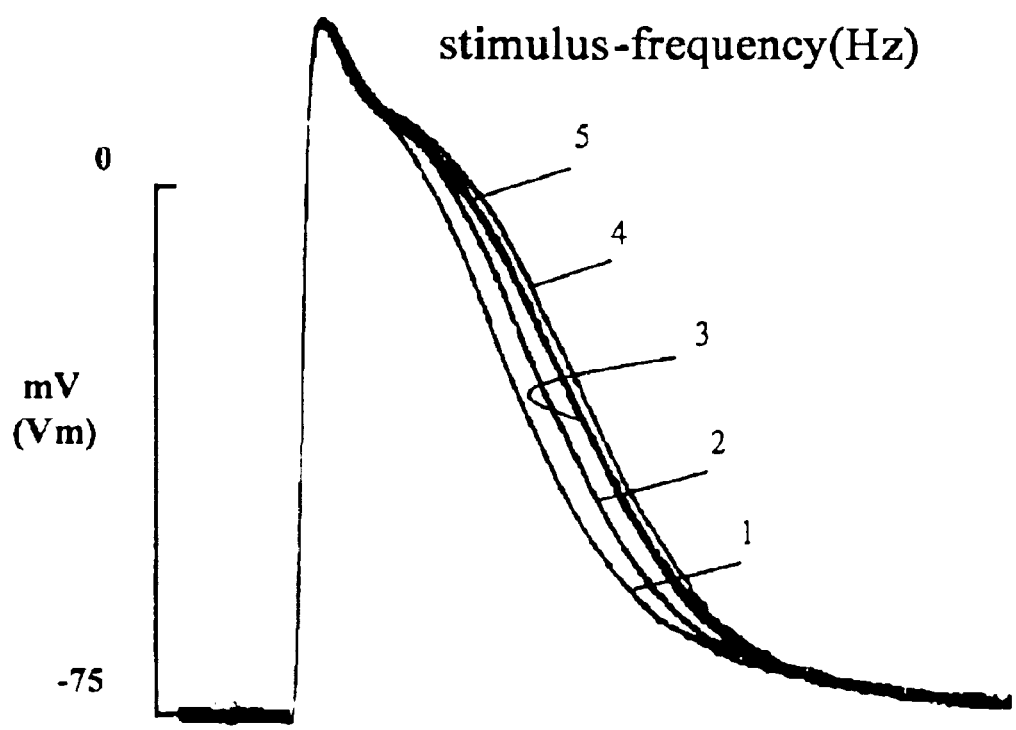
FIG. 5a shows representative tracings of action potentials in the absence of chelidonine (1 μM) under varied stimulus-frequencies.
Figure 5B:
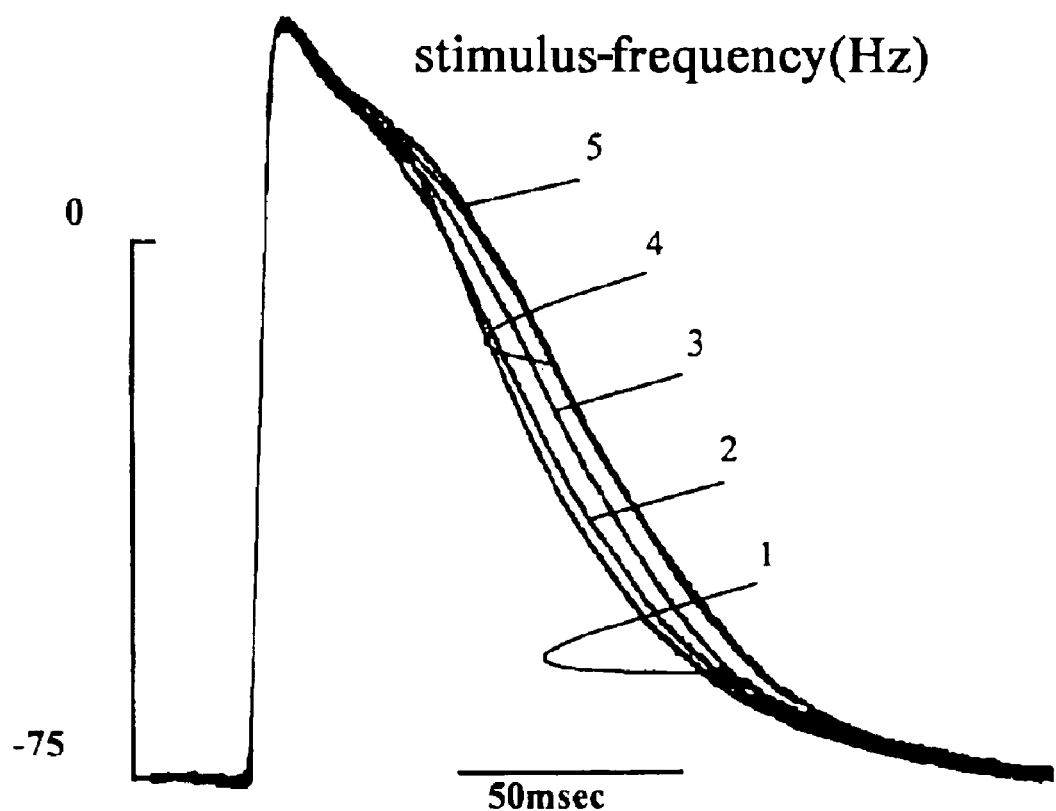
FIG. 5b shows representative tracings of action potentials in the presence of chelidonine (compound 1, 1 μM) under varied stimulus-frequencies.
Figure 5C:
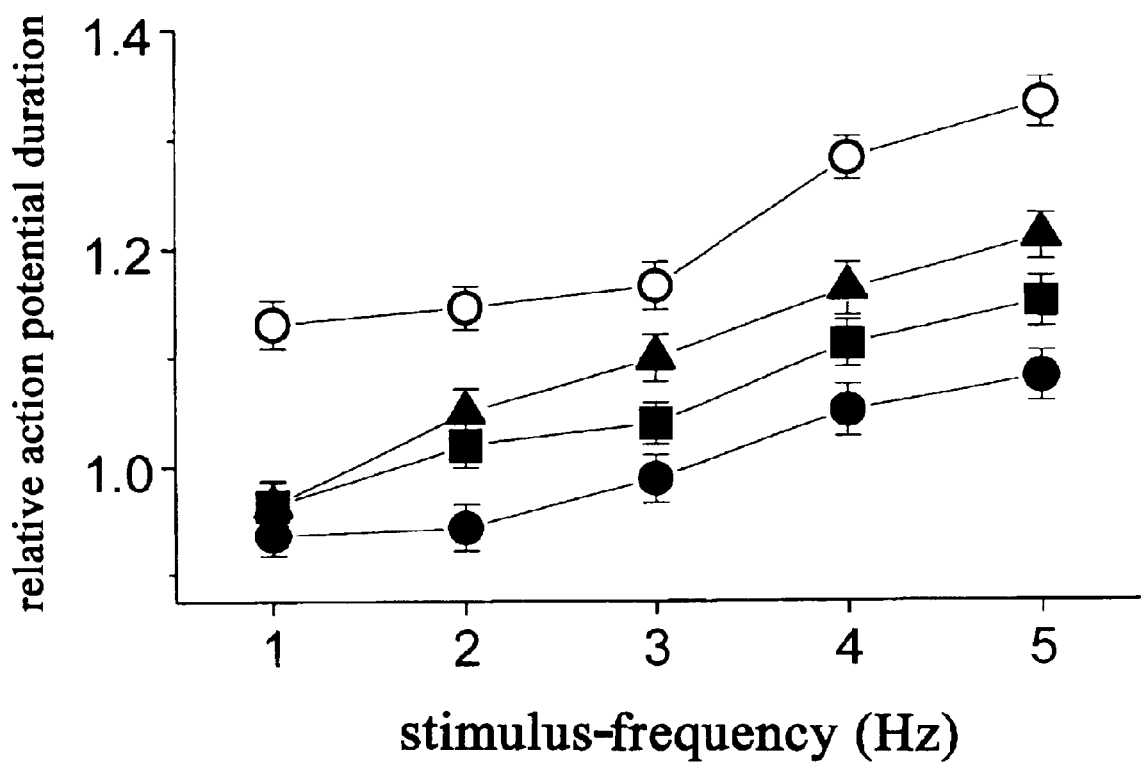
FIG. 5c shows averaged $APD_{90}$ (action potential duration at 90% repolarization) changes for action potential duration prolongation by chelidonine (compound 1, ○), acetylchelidonine (compound 4, ▲), benzoylchelidonine (compound 5, ■), and sanguinarine (compound 14, ●), respectively, under varied stimulus-frequencies.

FIGS. 5a (control) and 5b shows the representative tracings of action potentials on varied frequency in the absence (FIG. 5a) or presence (FIG. 5b) of chelidonine (compound 1), respectively. FIG. 5c shows averaged $APD_{90}$ (action potential duration at 90% repolarization) changes for action potential duration prolongations by chelidonine (compound 1, ○), acetylchelidonine (compound 4, ▲), benzoylchelidonine (compound 5, ■), and sanguinarine (compound 14, ●), respectively, depending on stimulus-frequencies. The relative action potential durations were normalized to the $APD_{90}$ value in the absence of chelidonine at each frequency. At the stimulus frequency of 1, 2, 3, 4 and 5 Hz, 1 μM chelidonine increased $APD_{90}$ by 13.0±8.1% (n=5), 14.5±7.9% (n=5), 16.5±2.2% (n=5) 28.2±0.4% (n=5) or 33.0±0.3 1% (n=5) of the control $APD_{90}$ in the absence of chelidonine at each frequency, respectively. Acetylchelidonine (compound 4), benzoylchelidonine (compound 5) and sanguinarine (compound 14) also increased the action potential durations in the similar manner as chelidonine, but to a lesser extent, compared to that of chelidonine (see, FIG. 5c).

In FIGS. 5, it was confirmed that chelidonine and derivatives thereof exhibit less antiarrhythmic activity at slow heart rates, but greater antiarrhythmic activity at fast heart rates. Therefore, it is expected that chelidonine and derivatives thereof are useful as ideal antiarrhythmic drugs with fewer side effects.

PREPARATIVE EXAMPLE 1

Tablet

A composition consisting of the following components was formulated into a tablet in accordance with a conventional process.

| Tablet composition | |
|---|---|
| Chelidonine | 500.0 mg |
| Lactose | 500.0 mg |
| Talc | 5.0 mg |
| Magnesium stearate | 1.0 mg |

PREPARATIVE EXAMPLE 2

Capsule

A composition consisting of the following components was formulated into a capsule in accordance with the following process:

First, the sieved chelidonine was mixed with an excipient. A capsule was prepared by filling gelatin capsule with the mixture.

| Capsule composition | |
|---|---|
| Chelidonine | 500.0 mg |
| Starch 1500 | 10.0 mg |
| Magnesium stearate | 100.0 mg |

PREPARATIVE EXAMPLE 3

Powder

The following components was mixed in accordance with a conventional process. The mixture was filled in an envelope and sealed to prepare a powder.

| Powder composition | |
|---|---|
| Chelidonine | 50.0 mg |
| Lactose | 100.0 mg |
| Talc | 5.0 mg |

PREPARATIVE EXAMPLE 4

Injection

A composition consisting of the following components was formulated into an injection in accordance with a conventional process. For example, the injection was prepared by filling a 2.0 ml ampoule with the composition and by sterilizing it.

| Injection composition | |
|---|---|
| Chelidonine | 50.0 mg |
| Antioxidant | 1.0 mg |
| Tween 80 | 1.0 mg |
| Distilled water for injection | to 2.0 ml |

INDUSTRIAL APPLICABILITY

The compositions according to the present invention have few problems with regard to safety and toxicity. In addition, the compositions according to the present invention can selectively block $K^+$ channels expressed in human atrial myocytes, and exhibit less antiarrhythmic activity at slow heart rates but greater activity at fast heart rates. Therefore, the compositions according to the present invention are useful as $K^+$ channel blockers and antiarrhythmic drugs.

What is claimed is:

1. A method for preventing or treating arrhythmias wherein the method comprises administering to a mammal a composition comprising a therapeutically effective amount of chelidonine or derivatives thereof represented by the following formula 1, with pharmaceutically acceptable carriers:

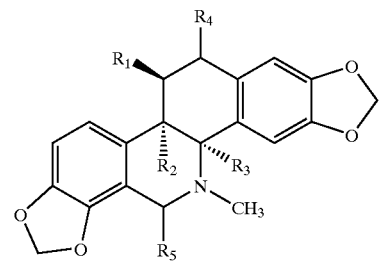

(1)

wherein, $R_1$ is selected from the group consisting of hydrogen, hydroxy, a lower alkoxy having 1 to 5 carbon atoms, benzyloxy, a lower alkylcarbonyloxy having 1 to 5 carbon atoms, benzoyloxy, a lower alkylsulfonyloxy having 1 to 5 carbon atoms, arylsulfonyloxy, diphenylphosphonyloxy, and —$OCONH_2$;

$R_2$ is hydrogen or methyl; and $R_3$, $R_4$ and $R_5$ are each, independently, hydrogen; or $R_1$ forms a double bond with $R_2$ or $R_4$; or $R_2$ forms a double bond with $R_3$; or $R_5$ forms a double bond with the adjacent N atom.

2. A method for preventing or treating $K^+$ channel-mediated myocardial diseases wherein the method comprises administering to a mammal a composition comprising a therapeutically effective amount of chelidonine or derivatives thereof represented by the following formula 1, with pharmaceutically acceptable carriers:

(1)

wherein,

R₁ is selected from the group consisting of hydrogen, hydroxy, a lower alkoxy having 1 to 5 carbon atoms, benzyloxy, a lower alkylcarbonyloxy having 1 to 5 carbon atoms, benzoyloxy, a lower alkylsulfonyloxy having 1 to 5 carbon atoms, arylsulfonyloxy, diphenylphosphonyloxy, and —OCONH₂;

R₂ is hydrogen or methyl; and

R₃, R₄ and R₅ are each, independently, hydrogen; or

R₁ forms a double bond with R₂ or R₄; or

R₂ forms a double bond with R₃; or

R⁵ forms a double bond with the adjacent N atom.

3. The method of claim 1 wherein R₁ is selected from the group consisting of hydrogen, hydroxy, methoxy, benzyloxy, acetoxy, benzoyloxy, methylsulfonyloxy, 4-methyl-benzenesulfonyloxy, diphenylphosphonyloxy and —OCONH₂; and R₂ is hydrogen or methyl; and R₃, R₄ and R₅ are each, independently, hydrogen; or R₁ forms a double bond with R₂ or R₄; or R₂ forms a double bond with R₃; or R₅ forms a double bond with the adjacent N atom.

4. The method of claim 1, wherein the chelidonine or derivative thereof is selected from the group consisting of:

[5bR-(5bα,6β,12bα)]-5b,6,7,12b,13,14,-hexahydro-13-methyl[1,3]benzodioxolo[5,6c]-1,3-dioxolo[4,5-i]phenanthridin-6-ol;

[5bR-(5bα,6β,12bα)]-5b,6,7,12b,13,14-hexahydro-6-methoxy-13-methyl[1,3]-benzodioxolo[5,6c]-1,3-dioxolo[4,5-i]phenanthridine;

[5bR-(5bα,6β,12bα)]-5b,6,7,12b,13,14-hexahydro-6-benzyloxy-13-methyl[1,3]benzodioxolo[5,6c]-1,3-dioxolo[4,5-i]phenanthridine;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-acetate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-benzoate;

(12bR)-13,14-dihydro-13-methyl[1,3]benzodioxolo[5,6c]-1,3-dioxolo[4,5-i]phenanthridine;

(12bR)-7,12b,13,14-tetrahydro-13-methyl[1,3]-benzodioxolo[5,6c]-1,3-dioxolo[4,5-i]phenanthridine;

[5bR-(5bα,6β,12bα)]-5b,6,7,12b,13,14-hexahydro-13-methyl[1,3]benzodioxolo[5,6c]-1,3-dioxolo[4,5-i]phenanthridine;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-diphenylphosphate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-methanesulfonate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-4-methylbenzenesulfonate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-carbamate;

[5bR-(5bα,6β,12bα)]-5b,6,7,12b,13,14-hexahydro-5b,13-dimethyl[1,3]-benzodioxolo[5,6c]-1,3-dioxolo[4,5-i]phenanthridin-6-ol; and 13-methyl[1,3]benzodioxolo[5,6c]-1,3-dioxolo[4,5-i]phenanthridinium.

5. The method of claim 1, wherein the pharmaceutically acceptable carrier includes at least one selected from the group consisting of excipients, binding agents, lubricants, disintegrating agents, coating agents, emulsifying agents, suspending agents, solvents, stabilizers, absorption agents, water for injection and isotonic agents.

6. The method of claim 1, wherein the composition is formulated into oral administration forms or injection administration forms.

7. The method of claim 1, wherein the composition is an antiarrhythmic drug.

8. The method of claim 1, wherein the composition is a K⁺ channel blocking agent.

9. The method of claim 8, wherein the composition is an hKv1.5 channel blocking agent.

10. The method of claim 2, wherein R₁ is selected from the group consisting of hydrogen, hydroxy, methoxy, benzyloxy, acetoxy, benzoyloxy, methylsulfonyloxy, 4-methyl-benzenesulfonyloxy, diphenylphosphonyloxy and —OCONH₂; and R₂ is hydrogen or methyl; and R₃, R₄ and R₅ are each, independently, hydrogen; or R₁ forms a double bond with R₂ or R₄; or R₂ forms a double bond with R₃; or R₅ forms a double bond with the adjacent N atom.

11. The method of claim 2, wherein the chelidonine or derivative thereof is selected from the group consisting of:

[5bR-(5bα,6β,12bα)]-5b,6,7,12b,13,14-hexahydro-13-methyl[1,3]benzodioxolo[5,6c]-1,3-dioxolo[4,5-i]phenanthridin-6-ol;

[5bR-(5bα,6β,12bα)]-5b,6,7,12b,13,14-hexahydro-6-methoxy-13-methyl[1,3]-benzodioxolo[5,6c]-1,3-dioxolo[4,5-i]phenanthridine;

[5bR-(5bα,6β,12bα)]-5b,6,7,12b,13,14-hexahydro-6-benzyloxy-13-methyl[1,3]benzodioxolo[5,6c]-1,3-dioxolo[4,5-i]phenanthridine;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-acetate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-benzoate;

(12bR)-13,14-dihydro-13-methyl[1,3]benzodioxolo[5,6c]-1,3-dioxolo[4,5-i]phenanthridine;

(12bR)-7,12b,13,14-tetrahydro-13-methyl[1,3]-benzodioxolo[5,6c]-1,3-dioxolo[4,5-i]phenanthridine;

[5bR-(5bα,6β,12bα)]-5b,6,7,12b,13,14-hexahydro-13-methyl[1,3]benzodioxolo[5,6c]-1,3-dioxolo[4,5-i]phenanthridine;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-diphenylphosphate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-methanesulfonate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-4-methylbenzenesulfonate;

{[5bR-(5bα,6β,12bα)]-5b,6,7,12b,13,14-hexahydro-13-methyl[1,3]benzodioxolo[5,6c]-1,3-dioxolo[4,5-i]phenanthridin-6-yl}-carbamate;

[5bR-(5bα,6β,12bα)]-5b,6,7,12b,13,14-hexahydro-5b,13-dimethyl[1,3]-benzodioxolo[5,6c]-1,3-dioxolo[4,5-i]phenanthridin-6-ol; and 13-methyl[1,3]benzodioxolo[5,6c]-1,3-dioxolo[4,5-i]phenanthridinium.

12. The method of claim 2, wherein the pharmaceutically acceptable carrier includes at least one selected from the group consisting of excipients, binding agents, lubricants, disintegrating agents, coating agents, emulsifying agents, suspending agents, solvents, stabilizers, absorption agents, water for injection and isotonic agents.

13. The method of claim 2, wherein the composition is formulated into oral administration forms or injection administration forms.

14. The method of claim 2, wherein the composition is an antiarrhythmic drug.

15. The method of claim 2, wherein the composition is a $K^+$ channel blocking agent.

16. The method of claim 15, wherein the composition is an hKv1.5 channel blocking agent.

* * * * *